United States Patent
Mehl, Sr. et al.

[11] Patent Number: 5,833,687
[45] Date of Patent: Nov. 10, 1998

[54] ELECTRICAL CURRENT HAIR REMOVAL TWEEZERS

[75] Inventors: Thomas L. Mehl, Sr., Rt. 1, 1015 Hwy 337, Old Bronson Rd, Newberry, Fla. 32669; George W. Harris, Jr., Palm Bay, Fla.

[73] Assignee: Thomas L. Mehl, Sr., Newberry, Fla.

[21] Appl. No.: 482,621

[22] Filed: Jun. 7, 1995

Related U.S. Application Data

[63] Continuation-in-part of Ser. No. 176,561, Dec. 30, 1993, Pat. No. 5,470,332, which is a continuation-in-part of Ser. No. 917,662, Jul. 20, 1992, abandoned, which is a continuation of Ser. No. 794,364, Nov. 13, 1991, abandoned, which is a continuation of Ser. No. 454,622, Dec. 21, 1989, abandoned, said Ser. No. 482,621, Jun. 7, 1995, is a continuation-in-part of Ser. No. 66,261, May 25, 1993, abandoned, which is a continuation-in-part of Ser. No. 929,750, Aug. 17, 1992, abandoned, which is a continuation-in-part of Ser. No. 707,828, May 30, 1991, abandoned.

[51] Int. Cl.[6] .................................................. A61B 17/41
[52] U.S. Cl. ................................................ 606/36; 606/43
[58] Field of Search ................................ 606/36, 43, 51, 606/52

[56] References Cited

U.S. PATENT DOCUMENTS

| 2,888,927 | 6/1959 | Fozard . |
| 4,174,714 | 11/1979 | Mehl ............................................. 606/43 |
| 5,049,148 | 9/1991 | Mehl ............................................. 606/43 |
| 5,221,280 | 6/1993 | Gross et al. . |
| 5,470,332 | 11/1995 | Mehl, Sr. et al. ........................... 606/43 |

FOREIGN PATENT DOCUMENTS

WO 95/17856  7/1995  WIPO .

*Primary Examiner*—Lee S. Cohen
*Attorney, Agent, or Firm*—Shlesinger, Arkwright & Garvey LLP

[57] ABSTRACT

A pair of insulated, clamping electrode electrical power output tweezers for hair removal, comprising a pair of normally closed, spaced opposed, conductive arms; a conductive tip disposed adjacent a free end of one of the pair of conductive arms; a non-conductive material substantially enclosing each one of the pair of arms; the non-conductive material defining a power transmission area disposed adjacent to and spaced from the free ends; and the power transmission area being substantially free of the non-conductive material and being sufficiently large for contacting hairs.

9 Claims, 3 Drawing Sheets

5,833,687

ELECTRICAL CURRENT HAIR REMOVAL TWEEZERS

CROSS-REFERENCE TO RELATED APPLICATIONS

This application is a continuation of International application Ser. No. PCT/US94/14557, filed Dec. 30, 1994, which is a continuation-in-part of application Ser. No. 08/176,561, filed Dec. 30, 1993, now U.S. Pat. No. 5,470,332, which is a continuation-in-part of application Ser. No. 07/917,662, filed Jul. 20, 1992, now abandoned, which is a continuation of application Ser. No. 07/794,364, filed Nov. 13, 1991, now abandoned, which is a continuation of 07/454,622, filed Dec. 21, 1989, now abandoned, and this application is a continuation-in-part of application Ser. No. 08/066,261, filed May 25, 1993, now abandoned, which is a continuation-in-part of application Ser. No. 07/929,750, filed Aug. 17, 1992, now abandoned, which is a continuation-in-part of application Ser. No. 07/707,828, filed May 30, 1991, now abandoned, and each of which is incorporated herein by reference.

FIELD OF THE INVENTION

This invention relates to a method for removing hair and for permanently impairing future hair growth, and an apparatus for carrying out this method.

BACKGROUND OF THE INVENTION

Inventors have long sought to permanently remove unwanted hair. Known techniques for hair removal are described in patents such as the following.

U.S. Pat. No. 5,364,394 to Mehl discloses a radio frequency (RF) hair removal method which effectively and permanently impairs future hair regrowth.

U.S. Pat. No. 4,174,714 to Mehl discloses a method for permanent removal of hair in which hair is removed and future hair growth is permanently impaired by grasping reduced lengths of a hair between conductive hair engaging surfaces, applying high frequency electrical waves to one of the conductive hair engaging surfaces, and holding the hair engaging surfaces in firm engagement in position against the skin and hair while applying the high frequency electrical waves until the hair releases. Although this method works well, there is a need for an even more efficient method of permanent hair removal.

U.S. Pat. No. 5,026,369 to Cole discloses a non-invasive method of removing hair through electrolysis in which a particular hair to be removed is cleaned, and then bathed in an electrode solution. A conductor is attached to a remote end of the treated hair after which a DC electrical current is directed down the electrode solution coating outside of the hair to the soft moist tissue surrounding hair within the skin, whereby sodium hydroxide (NaOH) in the hair follicle site is produced owing to the chemical reaction in the presence of electrical current for causing the hair follicle to die and allow the hair associated with the dead hair follicle to be removed.

U.S. Pat. No. 5,221,280 to Gross et al. discloses an electric hair removal device which automatically applies electric current to a hair being gripped until the gripped hair is plucked, at which time the current automatically terminates.

U.S. Pat. No. 5,049,148 to Mehl discloses a radio frequency hair removal tweezer including tweezer arms having facing interior surfaces including a radio frequency conducting hair engaging metal conducting pad for grasping hair to be removed. Although this hair removal tweezer operates well, there is a need for an effective hair removal method and apparatus which generate a variety of electrical outputs at the hair-engaging ends of the devices and which are even simpler and easier to use.

OBJECTS AND SUMMARY OF THE INVENTION

Accordingly, it is an object of the invention to provide a multiple hair removal method and apparatus for carrying out the method that are simpler to perform and to use than the known methods and apparatus.

It is another object of the invention to provide a hair removal method, system, and apparatus suited for removing one or more hairs at one time and which utilize all power outputs.

It is a further object of the invention to remove hairs easier and faster without stress and infection.

It is a still further object of the invention to provide a method and apparatus for permanent hair removal and impairment of hair regrowth.

It is an additional object of the invention to provide a hair removal system which has few moving parts, and which has interchangeable parts.

It is a further object of the invention to provide a hair removal system which is simple and which can be used by lay people.

It is yet another object of the invention to provide a method for permanent hair removal that uses an alkaline solution for pretreating the hair in order to more effectively increase the conductivity of hair than is possible with known neutral or acid-based systems.

It is yet another object of the invention to provide a method of permanent hair removal by which an alkaline solution is applied to the hair to be removed for opening the cuticle and cortex layers for causing all power outputs to penetrate the hair easier and faster.

It is a still further object of the invention to provide a method of multiple hair removal by which all treated hairs slide out of their respective treated follicles with substantially no resistance.

It is another object of the invention to provide a permanent multiple hair removal method and apparatus which can be used by non-professionals on their own skin.

It is a yet still further object of the invention to provide a permanent hair removal method and apparatus which make hair removal painless.

It is still another object of the invention to provide a permanent multiple hair removal system which shortens the time required for permanent hair removal.

It is another object of the invention to provide a permanent hair removal system which is less messy than conventional systems.

It is a further object of the invention to provide a substantially painless permanent multiple hair removal method and apparatus, unlike such as associated with traditional wax removal in which live hairs are pulled directly from the skin.

It is a still further object of the invention to provide for permanent multiple hair removal without the need for insertion of an electrolysis needle into the user's skin that causes burns and infection.

It is another object of the invention to provide a multipurpose conductive pair of tweezers which functions as a multiple-hair-removal tweezers, and as a single-hair-removal tweezers.

These and further objects of the invention will become apparent from the drawings and the following description of the invention.

It should be understood that all hair removal tweezer embodiments according to the invention can be used with all electrical power outputs.

It is to be understood that the terms "electrical output", "all power outputs" and "power generated at the hair-engaging end" of the tweezers, as used in describing the present invention, include: direct current (DC); alternating current (AC); radio frequency (RF); "blend", i.e., RF plus a DC component, or AC plus a DC component; and the like.

It is to be understood that the source of power to the hair removal tweezers may include all standard power sources such as "household current" (120 volt, 60 hertz, AC), DC, RF, and "blend" from a separate source.

DETAILED DESCRIPTION OF THE INVENTION

Figure 1:
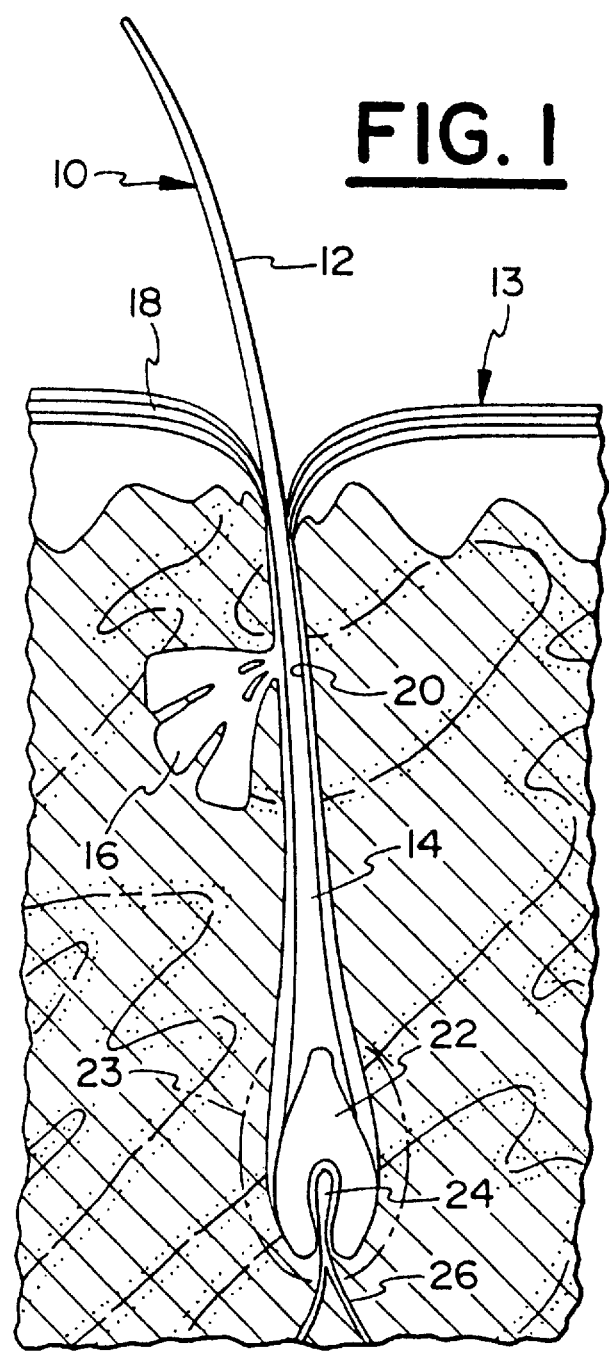
FIG. 1 is a schematic cross sectional view of a section of tissue showing a typical hair.

FIG. 1 is a representation of the manner in which hair is typically found. A hair 10 includes an upper shaft portion 12, which extends above a skin surface 13, and an interior lower shaft portion 14 extending beneath skin surface 13. Hair 10 passes adjacent to oil glands 16 disposed immediately below an epidermis area 18. Lower shaft 14 is connected to an external root sheath layer 20. The growth site for hair 10 is located in a matrix area 22. Matrix area 22 contains a papilla 24 supplied with nutrients by a blood vessel 26. Matrix area 22 and the cells 23 surrounding the follicle are the parts which must be reached and destroyed by electrical or chemical energy if future hair growth is to be prevented, given that all of the cells of the hair 10 above matrix area 22 are substantially dead fibrous material.

Accordingly, the target for an electrical current to be applied to hair 10 is essentially papilla 24, matrix area 22, and adjacent cellular structures.

It has been found that substantially dry hair 10 is not a sufficiently good electrical conductor for the present purposes. Hair becomes a better conductor when moisture is allowed to be absorbed into the hair shaft so that an electrical current can be induced. Then electrical current can be conducted from inner upper portion 12 to inner lower shaft portion 14 and, hence, the area around matrix 22.

Turning to FIGS. 2–6, insulated pairs of clamping electrode electrical power output tweezers or tongs 400 according to various preferred embodiments of the invention are illustrated.

Figure 2:
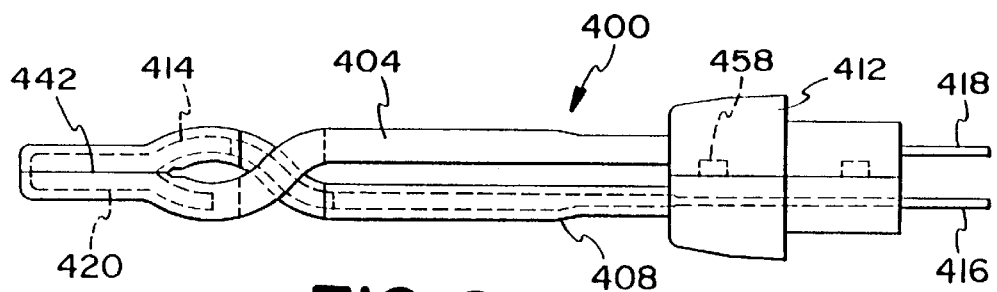
FIG. 2 is a top plan view of a preferred embodiment of conductive tweezers according to the invention.

FIG. 2 shows that insulated tweezers 400 preferably include an upper arm 404 normally biased against a lower arm 408. The terms "upper" and "lower" are used for expedience as the terms describe the relationship of arms 404 and 408 as viewed in FIG. 2, and are not intended to be limiting.

A base 412 is configured for insertion of any of the tweezer arm embodiments into a casing described below with regard to FIG. 6, for example.

A metal insert 414 extends substantially along almost the entire length of lower arm 408 and terminates in a free end or conductive extension 416. An opposed extension 418 can be made of metal or plastic, depending upon the intended use, as will be apparent from the description of the operation of tweezers 400 below.

A conductive metal insert 420 extends along a part of the length of upper arm 404; the illustrated pair of tweezers 400 is engineered particularly for use with an RF or blend (i.e., AC with a DC component, or RF with a DC component) power output.

Figure 3:
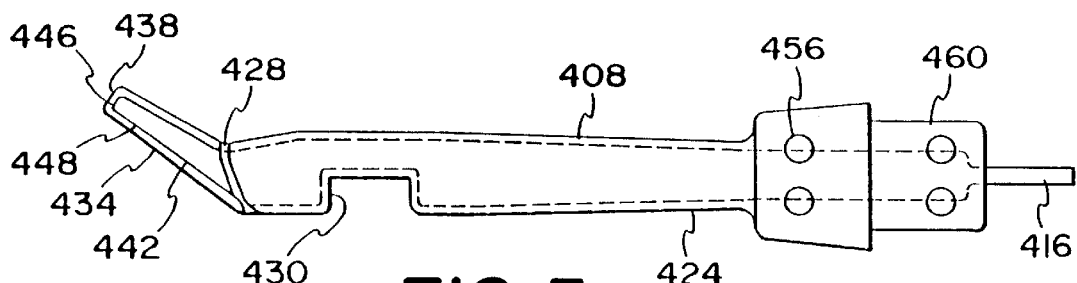
FIG. 3 is a side elevational view of one arm of the pair of tweezers of the preferred embodiment of FIG. 2.
Figure 4:
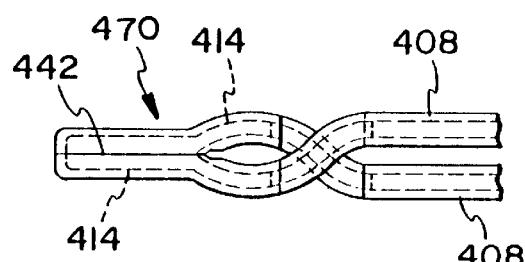
FIG. 4 is a top plan view of another preferred embodiment of conductive tweezers according to the invention.

As seen in FIGS. 3 and 4, lower arm 408 includes a plastic casing 424 which substantially completely surrounds metal insert 414.

As best seen in FIG. 3 an optional stepped portion 428 of plastic casing 424 demarcates a hair-grasping end 434 of arm 408. A "single" hair grasping free end 438 is defined at an outermost portion of hair-grasping end 434. A hair-contacting portion 442 of metal insert 414 is left partially uncovered by plastic casing 424.

Referring to both FIGS. 2 and 3, one can see that when tweezers 400 are in their normally closed position, hair-contacting portions 442 of opposed tweezer arms 404 and 408 will make contact. In use, hair-contacting portions 442 grasp respective portions of hairs to be treated. Hair-contacting portion 442 has a sufficiently short width at a "single" —hair contacting end 446 that one or two hairs can be conveniently grasped.

A multiple-hair grasping portion 448 of hair-contacting portion 442 is sufficiently long that multiple hairs can be grasped at the same time. Single-hair contacting portion 446 is surrounded by insulating material at 438 and elsewhere, so that exposed portion 442 will not contact the user's skin. Likewise, exposed portion 442 is set back from the free edge of insulating plastic casing 424 in the region of multiple-hair contacting region 448 so that the skin is not contacted by exposed portion 442; rather, only the hairs to be treated are grasped and contacted by exposed portion 442. One or more alignment bosses 456 are provided on one or both lower arms 408 for mating with respective seats 458 disposed in one or both arms 404.

A stepped base portion 460 extends from base 412.

Figure 5:
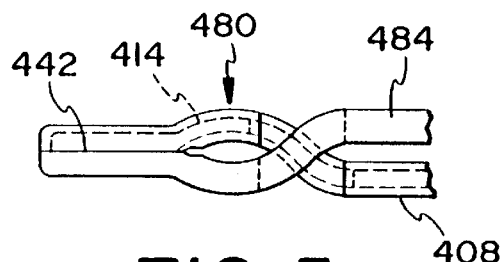
FIG. 5 is a top plan view of still another preferred embodiment of conductive tweezers according to the invention.

FIGS. 4 and 5 show additional embodiments, depending on the intended power source and particular application, of insulated tweezers 470 and 480, respectively, similar to insulated tweezers 400 of FIG. 2.

The FIG. 4 tweezers 470 have two opposing arms, each of which have full length conductive metal inserts 414 therein.

The FIG. 5 embodiment of tweezers 480 has two opposing arms, one of which has a full length conductive insert 414, with no metal insert at all in an opposed arm 484, for example.

Each one of upper arm 404 and lower arm 408 of the embodiment of FIG. 2, as well as each of the opposed arms of the embodiment of FIGS. 4 and 5, such as non-conductive arm 484, may be detachably attached to base 412.

Figure 6:
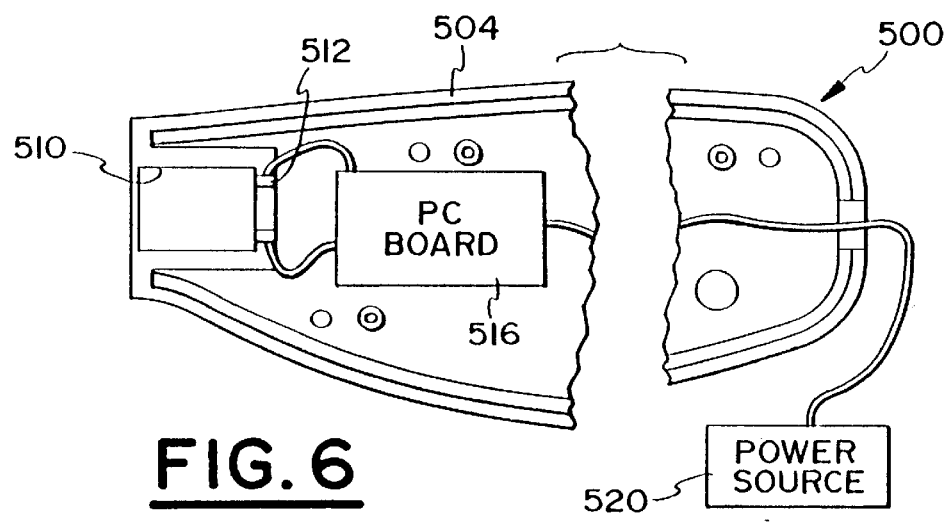
FIG. 6 is a top plan view of one half of a hand-held casing according to a preferred embodiment of the invention suitable for retaining and powering the various electrical sources to the pairs of tweezers of the embodiments of FIGS. 2–5; and, FIG. 7 is a perspective view of a direct current (DC) grounding unit according to a preferred embodiment of the invention.

FIG. 6 illustrates a hand-held casing 500 which is used for securing and powering insulated tweezers 400, 470, and 480, respectively of FIGS. 2–5. Hand-held casing 500 includes a plastic case 504 and a tweezers receptacle 510 configured for receiving stepped based portion 460. One or more female connectors 512 opens receive conductive extension 416 and extension 418. A conventional printed circuit (PC) board 516 converts and regulates the power supplied by a standard power source 520, such as a household alternating current (AC), into the desired level of direct current DC, AC, RF, or "blend" (e.g., AC with a DC component, or RF with a DC component) used in the hair removal system selected according to the invention.

Figure 7:
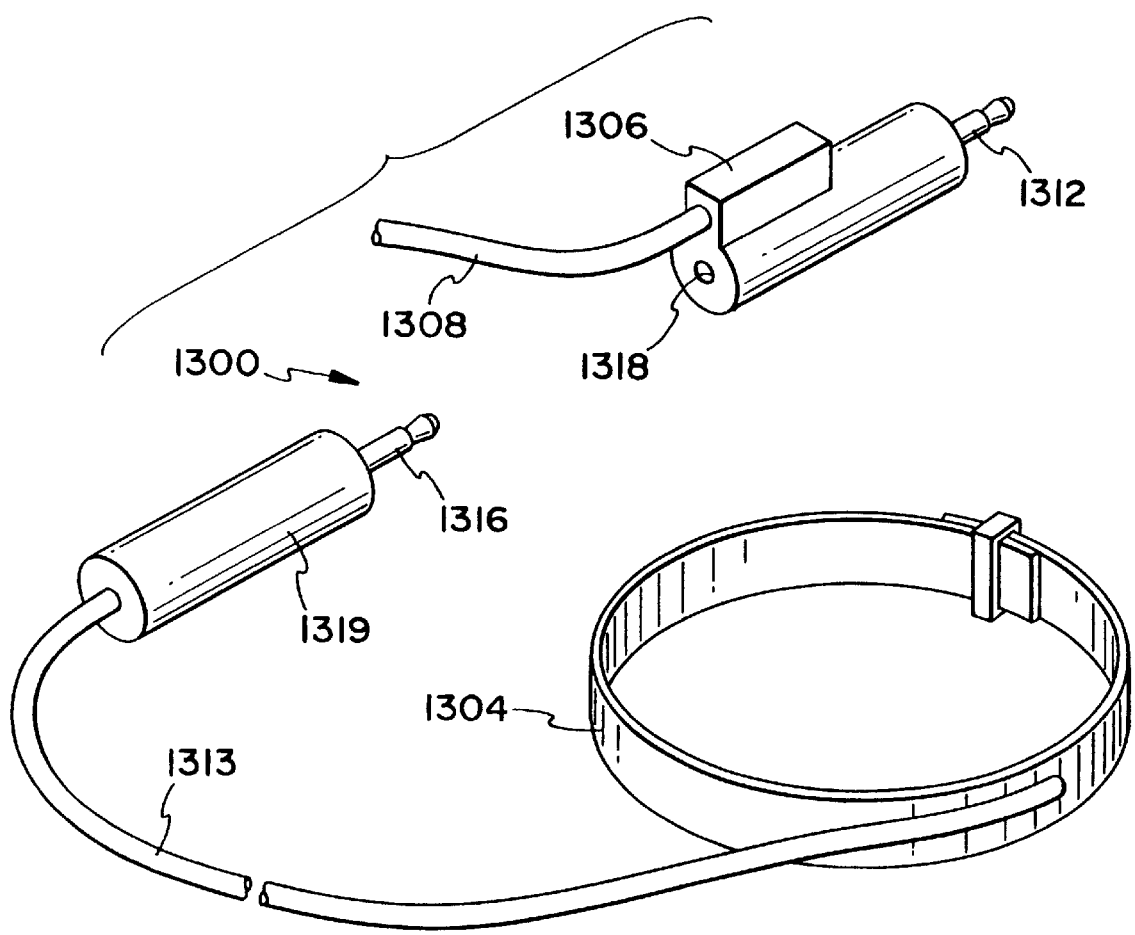

FIG. 7 illustrates a grounding accessory 1300 for use with all the hair removal embodiments of the invention, in the case where a DC power output is being used. When the person whose hair is being removed is working on himself or herself (e.g. the "patient" is the "user") the DC grounding accessory 1300 is unnecessary, as the patient will be grounded through the provision of a metalized casing or a metal conductive strip extending along the exterior of the casing that will contact the user's hand when grasping the casing.

When an operator of one of the DC power output accessories described above is someone other than the person whose hair is being removed, DC power output accessory 1300 will be used. A grounding strap 1304 is provided, which may conveniently be used as a wrist strap. If the patient being worked on holds the strap 1304 in his or her hand, sufficient grounding will typically be achieved. A DC power source/output piggy back connector 1306 includes an electrical connector 1308 which will be attached to the conventional transformer or other power source, in use. Piggy back connector 1306 includes a male connector 1312 which will be attached to the accessory being used (e.g., male connector 1312 will plug into a mating female receptacle in the casing of the hair treating devices (e.g. tweezers) described above for generating a DC output). A grounding cable 1313 extends from grounding strap 1304 and electrically connects to a male connector 1316. A connector body 1319 is grasped by the user when male connector 1316 is inserted into female connector 1318 of piggy back connector 1306 when grounding strap 1304 is used.

Good results have been achieved when a set of four (4) tweezer arms is provided with one (1) casing 500 so that the user can choose which one of the tweezer embodiments of FIGS. 2–5 to construct depending on the type of power to be output at the hair-engaging end of the tweezers. Thus, the four tweezer arms in a kit will typically include: two (2) arms 408 having full length conductive inserts that may be inserted into casing 500 in an opposed pair as shown in FIG. 4; one (1) arm 404 having a conductive metal insert, arm 404 being insertable into casing 500 in order to form an opposed pair with one of arms 408 as shown in FIG. 2; and one (1) arm 484 having no metal insert and being insertable into casing 500 in order to form an opposed pair with one of arms 408 as shown in FIG. 6.

OPERATION

Multiple hair removal tweezers 400 of FIG. 2 are used as follows.

Preferably, the skin having hair to be treated and removed is first steamed in order to both open the pores and to moisturize the hair for enhancing conductivity thereof.

A conductive solution, which may be a liquid, a gel, an emulsion, or a cream, is applied to the hair. The conductive solution is left in contact with the hair for a predetermined period of time. Preferably, the conductive solution has an alkaline formulation and a pH in the range of about 9 to 11. The length of the predetermined period of time is determined as described below, then the solution is wiped off.

Multiple hair removal tweezers 400 are used to grasp one or more hairs 10 at upper portion 12 thereof. Thus, hair 10 itself serves as a path by which power is transmitted from tweezer 400 to matrix root area 22 of the hairs to be destroyed.

Power source 520 is then turned on for a predetermined length of time. The predetermined period of time is a function of the number of hairs to be treated, the number of hairs to be destroyed, the physical attributes of the hair, the power level of the power output being used, and like considerations.

Accordingly, it is preferred that a preliminary test be done because the length of time required varies not only from person to person, but from one area of the body to another. Advantageously, a test area, commonly known as a "patch test" is done as it serves the additional purpose of determining whether the user is allergic to the conductive solution or to other constituents, and how well the roots and hairs accept the treatment.

For a fuller discussion of the chemical processes which are involved, attention is directed to U.S. Pat. No. 2,888,927 to Fozard; U.S. Pat. No. 4,174,714 to Mehl; U.S. Pat. No. 5,049,148 to Mehl; U.S. Pat. No. 5,364,394 to Mehl; and U.S. Pat. No. 5,026,369 to Cole described above, each of which is incorporated herein by reference.

For the application of DC power to kill the hair, the destroyed hair is allowed to remain in the body for a predetermined period of time, inasmuch as a chemical reaction has been started in the vicinity of matrix area 22 by the application of power thereto, and the chemical reaction continues at this site of hair growth for a period of time.

In order to optimize the length of time for which power is applied, one can conduct a test of the removed hairs so as to gauge the amount of destruction of matrix area 22.

This test is accomplished by use of a standard piece of litmus paper and distilled or deionized water. The piece of litmus paper is placed on the test bench, a drop of distilled and/or deionized water is applied, and the matrix area 22 of a removed hair is touched to the surface of the litmus paper.

A destroyed matrix area 22 will have undergone a chemical change sufficient that a spot on the piece of litmus paper to which matrix area 22 was touched indicates a pH in the range greater than about 7 (i.e., more in the alkaline range). Preferably, a relatively alkaline reaction will have occurred. Thus, typically, if the pH registers lower than about 8, the user simply increases the period of time for which power is applied.

The litmus test is repeated as required to determine the length of time necessary to properly treat single or multiple hairs.

In practice excellent results have been achieved when the application of DC power is for under 30 seconds, as it is the subsequent chemical reaction at matrix root area 22 that is typically the slower of the two steps. The subsequent chemical reaction at the matrix root area 22 may take about 30 minutes.

Tweezers 470 and 480 of FIGS. 4 and 5, respectively, are engineered to be used in multiple ways similar to the use of tweezer 400 of FIG. 2.

When tweezers 400 of FIG. 2 are used to supply power to the grasped hair or hairs to be treated, tweezers 400 can be inserted into hand-held casing 500 by mating extensions 416 and 418 with female connectors 512 as stepped base 460 engages tweezer receptacle 510. Power source 520 then supplies the required power to conductive extension 416, for example, the required power having been determined by PC board 516. The power output selected by the user (i.e., the power output determined by PC board 516) for the particular method is transmitted through metal insert 414 and through exposed portion 442 for supplying power to the grasped hairs. It will be appreciated that the power source and level for PC board 516 may be standard household current (e.g., 120 volt, 60 hertz, AC), a DC battery, a separate RF source, a separate "blend" source, and the like.

To open normally closed hair-grasping end 434, the user presses upper arm 404 toward lower arm 408 whereby the arms move relative to each other, facilitated by detent 430. Tweezers 400 are placed against the skin so that hair-grasping end 434 is near to the hairs to be removed. The plastic casing 424 defines the non-conductive regions surrounding exposed metal hair contacting portion 442; namely, a power transmission area is thereby defined.

When a DC output is generated at the tweezer end, the tweezer casing will typically be metalized or provided with a conductive metal strip on the exterior thereof.

Thus, when the user grasps the casing and turns on the device, the flow of electricity will be as follows: from the hair-grasping tip of the tweezers to the hair, from the hair to the body, from the body to the user's hand which is holding the metalized tweezer casing, and then back to the standard ground of the power source.

When an operator who is someone other than the person being treated is using the device, DC grounding accessory 1300 of FIG. 7 will be used when there is DC power output at the tweezer end. Thus, as described regarding FIG. 7 above, the person being treated (i.e., whose hair is being removed) will grasp grounding strap 1304 and the operator will grasp the metalized casing. Thus, in use, the flow of electricity will be from the tip of the tweezers to the hair being treated, from the hair to the treated person's body, from the body to the treated person's hand, from the treated person's hand to the grounding strap 1304, from grounding strap 1304 through grounding cable 1313 and thus, through male connector 1316, female connector 1318, and thus to the ground. Any "stray" DC power transmitted to the operator will go through the operator's hand to the metalized casing and then back to the standard ground of the DC power source.

The length of time during which the hair is allowed to stay in the body after the application of DC power varies and is preferably about 30 minutes. This time is generally adequate for the chemical reaction which has been induced by the application of power at matrix area 22 to continue sufficiently long for the so-called galvanic effect to take place, thereby leading to permanent impairment of future hair growth.

The above tweezers and associated hair removal methods effectively remove all treated hairs at this stage of growth.

In order to get complete and permanent hair removal, the above method steps will be repeated when the user can see hair stubble in the treated area resulting from hairs at different growth stages not removed by the first treatment. Additional treatments may be required as new hair growth occurs that may be induced by hormonal changes and the user's life cycle.

Different sizes of the multiple hair removal tweezers may be used depending on the body area, and whether the intended use is for an initial treatment when the removal of large numbers of hairs is required, or smaller tweezers may be used when follow-up treatments are performed or when only a small area of the skin is to be treated.

While this invention has been described as having a preferred designs, it is understood that it is capable of further modifications, uses and/or adaptations of the invention following in general the principle of the invention and including such departures from the present disclosure as come within the known or customary practice in the art to which to invention pertains and as may be applied to the central features hereinbefore set forth, and fall within the scope of the invention and of the limits of the appended claims.

What is claimed is:

1. A kit of insulated, electrical power output tweezers for hair removal, said kit of electrical power output tweezers comprising:
   a) a casing configured for receiving and orienting a pair of spaced opposed tweezer arms;
   b) at least one first insulated tweezer arm having a first conductive insert extending along substantially the entire length thereof;
   c) said first conductive insert including a first conductive hair-contacting portion;
   d) a second insulated tweezer arm having a second conductive insert disposed substantially only at a free hair-engaging and thereof;
   e) said second conductive insert including a second conductive hair-contacting portion;
   f) a third insulated tweezer arm being substantially non-conductive; and,
   g) each one of said tweezer arms being insertable into said casing.

2. A kit of tweezers as defined in claim 1, wherein:
   a) said at least one first insulated tweezer arm includes two first insulated tweezer arms each having a respective first said conductive insert extending substantially along the entire length thereof;
   b) each said first conductive insert including a respective first said conductive hair-contacting portion.

3. A kit of tweezers as defined in claim 2, wherein:
   a) at least one of said first and second conductive inserts is sufficiently large to contact a plurality of hairs.

4. A kit of tweezers as defined in claim 2, wherein:
   a) a grounding strap is provided for attachment to said tweezers; and
   b) said grounding strap is configured for being grasped by an operator.

5. A kit of tweezers as defined in claim 1, wherein:
   a) a power source is provided in said casing for providing an electrical power output to a tweezer arm received in said casing.

6. A kit of tweezers as defined in claim 1, wherein:
   a) a power source is provided externally of said casing for providing an electrical power output to a tweezer arm received in said casing.

7. A kit of tweezers as defined in claim 1, wherein:
   a) at least one of said first and second conductive inserts is sufficiently large to contact a plurality of hairs.

8. A kit of tweezers as defined in claim 1, wherein:
   a) at least one seat is provided on said casing; and
   b) a boss is provided on at least one of said first, second, and third tweezer arms for mating with said at least one seat when said at least one tweezer arm is inserted into said casing.

9. A kit of tweezers as defined in claim 1, wherein:
   a) said casing is configured for orienting said pair of spaced opposed tweezer arms in a normally closed position when received in said casing.

* * * * *